US006395692B1

(12) United States Patent
Jaworski et al.

(10) Patent No.: US 6,395,692 B1
(45) Date of Patent: *May 28, 2002

(54) MILD CLEANSING BAR COMPOSITIONS

(75) Inventors: Robert J. Jaworski, Scottsdale; Debra A. Park, Mesa, both of AZ (US)

(73) Assignee: The Dial Corporation, Scottsdale, AR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 101 days.

(21) Appl. No.: 08/726,089

(22) Filed: Oct. 4, 1996

(51) Int. Cl.$^7$ .................................................. A61K 7/50
(52) U.S. Cl. ...................... 510/147; 510/152; 510/155; 510/141
(58) Field of Search .................................. 510/130, 141, 510/147, 152, 155, 156

(56) References Cited

U.S. PATENT DOCUMENTS

| | | |
|---|---|---|
| 3,903,008 A | 9/1975 | Deweever |
| 3,969,259 A | 7/1976 | Lages |
| 4,165,293 A | 8/1979 | Gordon |
| 4,256,600 A | 3/1981 | Lewis |
| 4,290,904 A | 9/1981 | Poper |
| 4,297,230 A | 10/1981 | Rasser |
| 4,310,479 A | 1/1982 | Ooms |
| 4,468,338 A | 8/1984 | Lindberg |
| 4,490,280 A | 12/1984 | Joshi |
| 4,493,786 A | 1/1985 | Joshi |
| 4,517,107 A | 5/1985 | Clarke |
| 4,584,126 A | 4/1986 | Joshi |
| 4,673,525 A | 6/1987 | Small |
| 4,678,593 A | 7/1987 | Ridley |
| 4,719,030 A | 1/1988 | Williams |
| 4,741,854 A | 5/1988 | Krupa |
| 4,758,370 A | 7/1988 | Jungermann |
| 4,762,642 A | 8/1988 | Joshi |
| 4,851,147 A | 7/1989 | Esposito |
| 4,874,538 A | 10/1989 | Dawson |
| 4,879,063 A | 11/1989 | Wood-Rethwill |
| 4,923,627 A | 5/1990 | Joshi |
| 4,963,284 A | 10/1990 | Novakovic |
| 4,985,170 A | 1/1991 | Dawson |
| 4,988,453 A | 1/1991 | Chambers |
| 5,002,685 A | 3/1991 | Chambers |
| 5,041,234 A | 8/1991 | Instone |
| 5,082,600 A | 1/1992 | Smith |
| 5,217,639 A | 6/1993 | Mottola |
| 5,246,614 A | 9/1993 | Baumgartner |
| 5,262,079 A | * 11/1993 | Kacher et al. ............... 252/112 |
| 5,310,495 A | 5/1994 | Hill |
| 5,496,489 A | * 3/1996 | Dussault et al. ............ 252/134 |
| 5,520,840 A | * 5/1996 | Massaro et al. ....... 252/174.17 |

FOREIGN PATENT DOCUMENTS

EP 89310249.1 4/1990

* cited by examiner

*Primary Examiner*—Necholus Ogden
(74) *Attorney, Agent, or Firm*—Richard G. Harrer

(57) ABSTRACT

A transparent cleansing bar which includes a synthetic detergent, a major portion of which is a sulfated ethoxylated long chain alkyl alcohol, a polyhydric alcohol, a water soluble soap, a fatty acid alkanolamide, and optionally an alkylsarcosinic acid and an alkyl polyglycoside and wherein the pH is not less than about 8.0.

10 Claims, No Drawings

MILD CLEANSING BAR COMPOSITIONS

FIELD OF THE INVENTION

This invention relates to cleansing compositions for human use and more particularly to a cleansing composition in solid or bar form which is highly transparent, of exceptional mildness, and which will accept and is compatible with a variety of skin benefiting additions such as sunscreens, proteins, emollients and the like without adversely affecting the clarity of the composition.

BACKGROUND OF THE INVENTION

Translucent or substantially transparent soap bars have been available for consumer use for a number of years. These soap bars are generally glycerine-based or alcohol-based to obtain the desired clarity and contain high levels of sodium and/or potassium stearate, usually 65 percent or more, and when dissolved in water exhibit alkaline pH's of 8.5 or more and usually at least 9.5. These soaps have been said to be substantially less irritating than conventional non-translucent or non-transparent soap bars which contain from 65 to 95 percent sodium stearate and exhibit alkaline pH's ranging from 9.5 to 10.0. However, even the glycerine-based soap bars of pH's in the area of 9.5 or more have been found to be irritating to the skin and undesirable for use by those having particularly sensitive skin.

It has also been found that glycerine-based soap bars exhibit relatively high hygroscopic tendencies, that is they absorb water on the surface, which causes the bar's surface to slough and become scaly.

With respect to the alcohol-based soap bars, it has been found that alcohol evaporates from the bar over relatively short periods of time, thereby causing a reduction in size and clarity of the bar. The loss of alcohol may also cause the soap bar to become rubbery.

In formulating transparent soap, a classic method involves the low temperature saponification of fats and oils predissolved in warm alcohol, water and glycerine, followed by evaporation of part of the alcohol/water azeotrope. Another common technique is based upon the addition of a polyhydric alcohol, such as glycerol, glycol, sugar or the like to a "neat soap" or semi-boiled soap, or to soap prepared by the cold process technique. Still another method consists of dissolving soap in alcohol to solubilize certain components and then distilling off most of the alcohol.

U.S. Pat. No. 3,562,167 to Kamen describes a transparent soap formed from a combination of soap, polyhydric alcohol and, as a surface-active agent, a polyalkoxy ether of an alkylphenol.

U.S. Pat. No. 3,903,008 to Deweever et al describes the formulation of a transparent soap by the combination of soap, polyhydric alcohols and a quaternized dihydroimidazole detergent.

U.S. Pat. Nos. 3,793,214 and 3,926,828 to O'Neil et al describes transparent soaps produced using branched chain fatty acids. U.S. Pat. No. 3,864,272 to Toma et al, describes the use of a rather elaborate mechanical method of working the soap, i.e., spray drying followed by mechanical working to effect transparency.

A method of formulating a transparent soap is disclosed in U.S. Pat. No. 2,820,768 where a sodium soap made from tallow, coconut oil and castor oil is mixed with a triethanolamine soap of stearic acid, an oleic acid and an excess of the amine.

U.S. Pat. No. 4,290,904 describes a transparent low alkalinity bar soap based on a tetrakis (hydroxyalkyl) ethylene diamine.

U.S. Pat. No. 4,165,293 to Gordon discloses a solid transparent soap utilizing a high sodium soap content (about 55%) with a dihydric alcohol along with the anionic or amphoteric surfactant.

U.S. Pat. No. 4,719,030 to Williams et al describes a transparent soap bar using a water-insoluble synthetic amorphous silica or silicate having a specific surface area.

U.S. Pat. No. 4,851,147 to Esposito et al discloses a transparent soap using certain alkyl-aryl polyoxyalkalene carboxylic acids, a synthetic detergent, benzoic acid esters of primary alcohols and fatty acid soap.

A disadvantage of many of the early prior art transparent soap bars is that they form the typical scum in hard water. In order to overcome this problem with soaps in general, not only in transparent soaps, synthetic detergents were developed. It has been found, however, that when these synthetic detergents were added to the typical transparent soap to form what is called a "combo-bar" (i.e., a combination of synthetic detergent and soap), transparency is a problem. To our knowledge, no one to date has made a transparent bar using a synthetic detergent and a soap having the enhanced transparency, clarity, and mildness described and claimed herein.

SUMMARY OF THE INVENTION

Accordingly, the present invention provides a cleansing bar composition and the process for its manufacture, the bar being transparent, that is of exceptionally high clarity, exceptional mildness and which employs no monohydric alcohol, sugar or amines as may be found in many transparent bar compositions. The bar has excellent color stability and can accept a number of skin benefiting additives without adversely affecting its clarity.

In a preferred embodiment, the cleansing bar composition comprises the following major components:

1. From about 10 to 45 weight % of a synthetic detergent, the principal synthetic detergent component being:

a. from 15% to 35% a salt of a sulfated ethoxylated long chain alkyl alcohol that conforms generally to the formula:

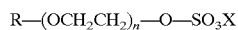

$$R\text{—}(OCH_2CH_2)_n\text{—}O\text{—}SO_3X$$

where R=an alkyl group having from 12 to 16 carbon atoms,
   wherein n=2 or 3; and x is an alkali metal or alkaline earth metal such as sodium, potassium, lithium, magnesium, barium, and ammonium ($NH_4^+$).

b. Additionally from about 0 to 10% by weight of a nonionic alkyl polyglycoside having the general formula

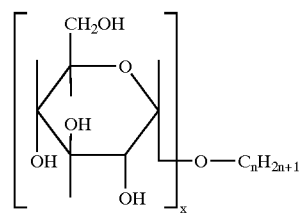

wherein x is greater than 1 and less than 2;

c. and from about 0 to 15% by weight of an alkyl sarcosinic acid having the formula:

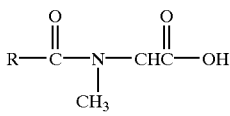

where R is alkyl having from 10 to 16 carbon atoms, preferably cocoyl.
2. From 10 to 30% by weight of a polyhydric alcohol such as propylene glycol, glycerol, sorbitol and a polyethylene glycol having the formula:

wherein n has an average value of 6 to 16, preferably 12.
3. From 15 to 30% by weight of a water soluble soap which is preferably formed in situ by the reaction of long chain fatty acids with an alkali such as sodium hydroxide. The ratio of water soluble soap to synthetic detergent should range from to 1:1 to 1:2.
4. From 5 to 20% of a foam/lather stabilizer, preferably the diethanolamides of fatty acids such as capric and the fatty acids derived from coconut oil.
5. The balance being perfume, colorants, skin benefiting additives and water.

With respect to the synthetic detergent components of this composition, the principal detergent is a salt of a sulfated ethoxylated fatty alcohol having the formula:

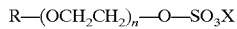

and a preferred material is where R is lauroyl, n is 3 and X is sodium, the compound being sodium laureth sulfate (CTFA). Although sodium laureth sulfate has been found to be more irritating to the skin than, for example, sodium cocoyl isethionate, which is found in many so called "mild" cleansing composition, when used in conjunction with the other components of our composition and in the specified ratios, the composition of this invention is found to be at least equal to the benchmark of toilet soaps in mildness to the skin and milder than existing commercial transparent cleansing bar products. It is also of interest to note that a preferred bar composition of this invention has a pH of about 9.6 whereas the pH of the leading "mild" cleansing bar ranges from about 6.5–7.0. Since there is usually some correlation between pH and skin irritation, with the product having the lower pH being milder, it is surprising to find that our product, even with a relatively high pH, is equal in mildness to the lower pH product. In fact, it is better that the pH of our composition not be below 7.5 and preferably not below 8.0 as pH's below these levels can cause a loss in hardness and clarity in the composition.

As shown the synthetic detergent component may also include a relatively minor amount of an alkyl polyglycoside. Since the bar composition is processed by a hot melt technique as will be explained later, the presence of the glycoside serves to reduce the temperature of the ultimate mixture by up to about 10° F. which aids in the packaging and perfuming of the product. A preferred glycoside is available from Henkel Corporation as Plantaren 2000, and a preferred level is from about 1 to about 3 weight % of the composition.

It is also preferable to include from about 5 to 10% by weight of an alkyl sarcosinic acid, a preferred material being N-cocoyl sarcosine or cocoyl sarcosinic acid. We find that the addition of this material speeds up lather formation and also has a detergent function.

The second principal component of the composition is a water soluble soap such as sodium stearate which is preferably formed in situ by the reaction of long chain fatty acids with an alkali such as sodium hydroxide. The particular fatty acids employed are not critical and may be varied depending on the bar hardness desired. We prefer stearic acid since its use results in a harder bar and also prefer to use, along with the stearic acid, a minor amount of capric acid which serves to boost lather production. Although it is preferred to form the water soluble soap in situ, a previously formed soap such as sodium stearate, can be added to the mixture. However, we have found that forming the soap in situ results in a beneficial lowering of the processing temperature by about 10° F. and a rather substantial reduction in processing time. It is important that the ratio of synthetic detergent to water soluble soap range from about 1:1 to 1:2, with a ratio of about 4:5 being preferred. In order to obtain acceptable bar hardness, the amount of soap present in the composition should be at least about 17% by weight and preferably about 18% by weight or more.

Another principal component of the transparent cleansing bar is a polyhydric alcohol to promote clarity of the product. Such alcohols as propylene glycol, glycerol, sorbitol and a polyethylene glycol such as PEG-12 (CTFA) can be used, it being preferred that a substantial amount of the alcohol used be propylene glycol since we find it promotes clarity of the bar to a greater extent than other of the useful alcohols. It is important that the amount of polyhydric alcohol present in the composition be at least as great as the amount of soap present and preferably somewhat in excess of the amount of soap, i.e., about at least 1.25 parts of glycol to 1 part of soap.

The composition also includes from about 5 to 20% by weight of a foam and lather enhancing agent and preferably fatty acid alkanolamides are used. Examples of suitable fatty acid alkanolamides include myristic diethanolamide, lauryl-myristal diethanolamide, capric diethanolamide, coconut diethanolamide and lauric diethanolamide. Preferred is capric diethanolamide or coconut diethanolamide. Preferably about 10 to 15% by weight of the composition is a fatty alkanolamide.

Another important advantage of the composition of this invention is its ability to solubilize a number of supplemental skin benefiting ingredients without adversely affecting the clarity and performance of the cleansing bar. Such supplemental ingredients include proteins of both animal and plant derivation, phospholipids, sunscreen agents, mucopolysaccharides, derivatives of polyvinyl pyrollidone, vitamin derivatives and certain cationic guar gums. A preferred guar gum is available from Rhone-Poulenc, Inc. and designated as Jaguar C-162. Table III identifies a number of such supplemental skin benefitting ingredients, the level at which each was incorporated in a cleansing bar composition and their purpose.

The basic process for making the cleansing composition according to the invention uses a "hot melt" procedure which involves mixing and heating of the various ingredients and thus requires no milling, plodding, or drying equipment. The process comprises initially mixing, at room temperature and at low agitation, all liquid ingredients (excepting caustic or those sensitive to caustic) in a vessel; such ingredients include water, polyhydric alcohols, fatty acid diethanolamides and alkyl sarcoscinic acid. As mixing proceeds, the temperature is slowly increased to about 120° F., at which point the synthetic detergent sodium laureth sulfate is added. When addition is complete, the temperature is increased to about 160° F. At this point sodium stearate, if used, or the fatty acids are added and the temperature of the mixture is increased to about 170° F. and the alkali (solution of sodium hydroxide) is added. The stir rate of the reaction mixture should be increased to facilitate the formation and dissolution of the sodium soaps thus formed. The temperature is allowed to rise to about 200° F. at which point any dye may be added. This 200° F. temperature is maintained until all the soap has gone into solution. Heating is then stopped, and when the temperature drops below about 190° F., any perfume or liquids sensitive to the caustic are added. The reaction mixture is allowed to cool to about 175–185° F. and the mixture is ready to be poured into molds.

The molten composition may be poured into a preformed package having a cavity of desired shape, followed by cooling of the composition to form a solid bar in the package. An advantage of such process is that the preform package serves both as the mold and package for the product, eliminating the need for wrapping equipment and special dies.

Another method involves introducing the liquid mixture into frames which is well known in the art. Customarily, after solidification has taken place, the solid composition may be cut into a desired size using cutting apparatus known in the soap-making art, such as heated wire cutters. The bars so produced are then wrapped and cartoned for shipment.

An alternative preferred method of forming the cleansing composition of the invention into bars, comprises the steps of dispensing the molten composition using liquid-fill apparatus into a mold having a cavity of desired shape, cooling the composition until it solidifies in the mold, removing the solidified composition from the mold, and stamping the molded composition into a bar. The last step, stamping the molded composition into a bar, is not an essential step, as the molded composition could be packaged for sale straight from the mold without further stamping, although stamping is preferred to give the bar a desirable finished shape and polish, and to imprint a desired trademark, logo, or other design in the bar.

To evaluate the mildness of the compositions of this invention a modification of the procedure described by Frosh and Kligman in: "The Soap Chamber Test", *Journal of the American Academy of Dermatology* 1:35–41, 1979 was employed. In this procedure, approximately 20 panelists are randomly selected from men and women, who are 18 years of age and over and who have not participated in any other skin irritation test of this nature for six weeks nor have experienced a hypersensitivity to a test material in the last six months. Panelists are screened so as not to have any skin disorders such as eczema, psoriasis, and the like. Panelists taking any medication on a regular basis, such as anti-inflammatory agents, steroids, cortisones, aspirin, antihistamines, topical ointments/creams, are not selected. Prior to acceptance into the study, each panelist was interviewed to obtain pertinent medical and habitual information.

A 19 mm diameter aluminum cup called a chamber is employed. Two layers of a nonwoven cotton cloth (Webril discs available from Curity) are snugly fitted into the chamber which receives the various test solutions. The test materials are 8% solutions of the compositions to be tested and are prepared daily. If required, the chambers can be secured to the skin with a non-occlusive tape.

The Webril discs are moistened with approximately 0.1 ml of test materials and applied to the panelist's forearm according to a randomization schedule for each subject. A maximum of six chambers is applied to each arm of each panelist. The five-day test is scheduled so as to begin on Monday and end on Friday. The initial patch remains on for a 24-hour period; patches applied Tuesday will remain on for 5 hours, patches applied Wednesday through Friday will remain on for a 6-hour period. Subjects are instructed to keep the patches dry. Patches are removed and test sites are rinsed with tap water 1/2 hour prior to scoring.

Scoring takes place on Tuesday morning and Tuesday through Friday afternoons according to th e following scales:

Redness
  0=No reaction
  1=Spotty, skin discoloration not red (follicular or diffuse)
  2=Slight redness
  3=Moderate, uniform redness
  4=Fiery redness (covering total area and beyond)
Edema
  0=No reaction
  1=Slight edema
  2=Moderate edema
  3=Severe edema
Vesicles
  0=No reaction
  1=Few vesicles
  2=Many vesicles
  3=Numerous vesicles Subjects are questioned daily concerning any discomfort which occurred during the day or night. If the irritation level with any test product on a panelist reaches a grade greater than 2.0 using the vesicle scale or a total score of 7 at any time during the test, no product is applied for the remainder of the test to that site.

Tables I and II set out a variety of formulas for cleansing bars which were made according to the previously described process.

TABLE I

| | BAR | | | | | |
|---|---|---|---|---|---|---|
| INGREDIENT | Optimum A | W169 B | W170 C | W98 D | W94 E | W108 F |
| Sodium Stearate | | 20.0 | | 17.3 | 18.0 | 24.0 |
| Stearic Acid | 16.5 | | 18.5 | | | |
| Capric Acid | 2.0 | | | | | |
| Sodium Hydroxide (50%) | 5.84 | | 5.5 | | | |
| Sodium Laureth -3 Sulfate (70%) | 25.0 | 26.0 | 26.0 | 26.0 | 27.0 | 30.0 |
| Cocoyl Sarcosinic Acid | 1.5 | 2.0 | 2.0 | | | |
| Propylene Glycol | 12.0 | 12.0 | 12.0 | 10.4 | 11.0 | 12.0 |
| PEG-12 | 6.1 | 8.0 | 8.0 | | | |
| Glycerin | 4.6 | 6.0 | 6.0 | 4.3 | 4.8 | 4.5 |
| Sorbitol (70%) | 4.6 | 6.0 | 6.0 | | | |
| Cocoamide DEA | 6.1 | 8.0 | 8.0 | | 9.0 | 10.0 |
| Capramide DEA | 3.0 | 4.0 | 4.0 | | | |
| PEG-60 Almond Glyceride | 3.0 | | | | | |
| Behenamidepropyl PG Dimonium chloride (30%) | 3.0 | | | | | |
| Alkyl Polyglycoside Plantaren 2000 (50%) | 2.0 | | | | | |
| Polyquaternium-7 (8%) | 0.5 | | | | | |
| Water | 3.0 | 8.0 | 3.0 | 4.3 | 4.5 | 8.0 |

TABLE I-continued

| | BAR | | | | | |
|---|---|---|---|---|---|---|
| INGREDIENT | Optimum A | W169 B | W170 C | W98 D | W94 E | W108 F |
| Cocoamide DEA | | | | 9.1 | 9.0 | 10.0 |
| Cocoyl Sarcosinate | | | | | | |
| Cocoamidopropyl Betaine (35%) | | | | 8.7 | 5.0 | |
| Isostearamidopropyl Morpholine Lactate (25%) | | | | 2.6 | 2.0 | |
| PEG-6 | | | | 8.7 | 9.0 | |
| Cocoamide DEA/DEA Laureth Sulfate | | | | 8.7 | | |
| Citric Acid | | | | 1.0 | | 0.40 |
| Dye, Perfume | 1.26 | | 1.0 | | 0.9 | |

TABLE II

| | BAR | | | | | |
|---|---|---|---|---|---|---|
| INGREDIENT | W68 G | W153 H | W87 I | W104 J | W201 K | W204 L |
| Sodium Stearate | 20.0 | 19.4 | 20.0 | 20.0 | | |
| Stearic Acid | | | | | 16.5 | 16.6 |
| Capric Acid | | | | | 2.0 | 2.0 |
| Sodium Hydroxide (50%) | | | | | 5.8 | 5.8 |
| Sodium Laureth 3-Sulfate (70%) | 32.0 | 29.1 | 30.0 | 30.0 | 19.5 | 26.0 |
| Cocoyl Sarcosinic Acid | | | | | 2.0 | 2.0 |
| Propylene Glycol | 15.0 | 11.7 | 12.0 | 12.0 | 12.0 | 12.0 |
| PEG-12 | | 7.8 | | | 8.0 | 8.0 |
| Glycerin | 5.0 | 4.8 | 5.0 | 5.0 | 6.0 | 6.0 |
| Sorbitol (70%) | | | | | 6.0 | 6.0 |
| Cocoamide DEA | | 17.5 | | 9.0 | 8.0 | 8.0 |
| Capramide DEA | | | 5.0 | | 4.0 | 4.0 |
| PEG-60 Almond Glyceride | | | | | | |
| Behenamidopropyl PG Dimonium chloride (30%) | | | | | | |
| Alkyl Polyglycoside Planataren 2000 (50%) | | | | | 9.0 | 2.0 |
| Polyquaternium-7 (8%) | | | | | | |
| Water | 5.0 | 9.7 | 5.0 | 8.0 | | 0.7 |
| Cocoamide DEA Cocoyl Sarcosinate | | | 8.0 | | | |
| Cocoamidopropyl Betaine (35%) | 10.0 | | 10.0 | | | |
| Isostearamidopropyl Morpholine Lactate (25%) | 3.0 | | 3.0 | | | |
| PEG-6 | 10.0 | | 10.0 | 5.0 | | |
| Citric Acid | | | 0.4 | 3.0 | | |
| Dye, Perfumes | | | | | | |

Observations Regarding Bars in Tables I and II

1. Bars A, C, K and L were made utilizing in situ neutralization of the fatty acids. This lowered the processing temperatures slightly and resulted in a decrease of total time to process the bars.
2. Bar E was slightly firmer than Bar D because of the increase in the amount of soap (sodium stearate).
3. Bar F had the highest level of soap at 24% and was not satisfactory since the amount of glycol present (16.5%) was not sufficient to solubilize the soap (sodium stearate). Our findings indicate that the amount of glycol present should be slightly in excess of the amount of soap; most preferably at least about 1.25 parts of glycol to 1 part of soap.
4. The effect of pH was determined by comparing Bars I and J. Bar I had a relatively high pH of 9.0 and was a very satisfactory bar in all respects. Bar J had a pH of about 7.5 and was unsatisfactory since it was opaque and did not properly harden at room temperature.
5. The effect of the alkyl polyglycoside was demonstrated in Bars K and L. The pour point of the formulation used to make Bar K which contained 4.5% of the polyglycoside was reduced by about 10–15° F. The pour point of Bar L which contained 1% of the polyglycoside was not significantly changed.

Incorporation of Skin Benefitting Agents

Five (5) different skin benefitting agents were incorporated into the cleansing compositions of this invention at appropriate levels. Such compositions, including the agents used, are identified below. The bars were evaluated for transparency and it was determined that these ingredients did not have an adverse effect on this quality.

TABLE III

| MATERIAL | W186 | W193 | W200 | W205 | W222 |
|---|---|---|---|---|---|
| Stearic Acid | 16.5 | 16.5 | 16.5 | 16.5 | 16.5 |
| Capric Acid | 2.0 | 2.0 | 2.0 | 2.0 | 2.0 |
| Sodium Hydroxide (50%) | 2.9 | 2.9 | 2.9 | 2.9 | 2.9 |
| Na Laureth-3 Sulfate (70%) | 18.2 | 18.2 | 18.2 | 17.5 | 17.5 |
| Cocoyl Sarcosinic Acid | 2.0 | 2.0 | 2.0 | 2.0 | 2.0 |
| Propylene Glycol | 12.0 | 12.0 | 12.0 | 11.5 | 12.0 |
| PEG-12 | 8.0 | 8.0 | 8.0 | 7.6 | 8.0 |
| Glycerin | 6.0 | 6.0 | 6.0 | 5.8 | 6.0 |
| Sorbitol (70%) | 4.2 | 4.2 | 4.2 | 4.1 | 4.2 |
| Cocoamide DEA | 8.0 | 8.0 | 8.0 | 8.0 | 8.0 |
| Capramide DEA | 4.0 | 4.0 | 4.0 | 4.0 | 4.0 |
| Water | 13.4 | 14.9 | 13.4 | 12.3 | 13.9 |
| Caprylic/Capric Triglyceride | 2.0 | | | | |
| Vitamin E Linoleate | | 0.5 | | | |
| Dimethicone Copolyol | | | 2.0 | | |
| Octyl Methoxycinnamate | | | | 5.0 | |
| Hydrolyzed Animal Protein | | | | | 2.0 |
| Perfume | 0.8 | 0.8 | 0.8 | 0.8 | 1.0 |

| | |
|---|---|
| Hydrolyzed animal protein | Henkel Natrelan |
| Octyl methoxycinnamate | Parsol MCX |
| Dimethicone Copolyol | Dow Corning 193 surfactant |
| Vitamin E linoleate | Roche |
| Caprylic/Capric Triglyceride | Henkel Myritol 318 |

Mildness Assessments

Set forth in the following Tables IV–VIII are formulas for bar compositions of this invention and a mildness assessment for each according to the modified Frosh and Kligman "The Soap Chamber Test" as previously described. The formula for each bar evaluated and its "Mildness Score" is provided. The mildness score is an average of the redness score, edema score and vesicles score. The lower the number, the milder the bar.

TABLE IV

| INGREDIENT | W11 | W18 | W22 | W24 | W55 | W70 |
|---|---|---|---|---|---|---|
| Sodium Stearate | 24.0 | 24.0 | 24.0 | 24.0 | 20.0 | 21.7 |
| Stearic Acid | | | | | | |
| Capric Acid | | | | | | |
| Sodium Hydroxide (50%) | | | | | | |
| Na Laureth-3 Sulfate (70%) | | | | | 20.3 | 22.1 |
| Cocoyl Sarcosinic Acid | | | | | | |
| Propylene Glycol | 6.0 | 6.0 | 6.0 | 6.0 | 20.0 | 21.7 |
| PEG-12 | | | | 6.0 | | |
| Glycerin | 14.0 | 14.0 | 10.0 | 10.0 | 5.0 | 5.4 |
| Sorbitol (70%) | | | | | | |
| Cocamide DEA | 19.0 | 18.0 | 18.0 | 18.0 | 10.0 | 11.0 |
| Water | 15.6 | 15.0 | 18.6 | 17.6 | 20.5 | 17.3 |
| Sodium Lauroyl Sarcosinate | 5.4 | 6.0 | 6.0 | 7.0 | | |
| *Isostearamidopropyl Morpholine Lactate (25%) | 1.0 | 1.0 | 1.0 | 1.0 | 0.75 | 0.8 |
| *PPG-25 Diethylmonium Chloride | 5.0 | 4.0 | | | | |
| *PEG-6 | 10.0 | 6.0 | 6.0 | | | |
| Sodium Cocoyl Isethionate | | 5.0 | 5.0 | 5.0 | | |
| *C12–15 Alcohols Benzoate | | 1.0 | | | | |
| Disodium Ricinoleamido MEA Sulfosuccinate | | | 0.4 | 0.4 | | |
| *Cocamidopropyl Betaine | | | | 3.5 | | |
| *Ceteareth-30 | | | 5.0 | 5.0 | | |
| Mildness Score | 0.99 | 0.99 | 1.03 | 1.18 | 2.5 | 2.4 |

*Skin feel additive

TABLE V

| INGREDIENT | W105 | W102 | W124 | W114 | W190 | W172 |
|---|---|---|---|---|---|---|
| Sodium Stearate | 20.0 | 20.0 | 20.0 | 20.0 | | |
| Stearic Acid | | | | | 16.5 | 18.5 |
| Capric Acid | | | | | 2.0 | |
| Sodium Hydroxide | | | | | 2.9 | 2.8 |
| Na Laureth-3 Sulfate | 19.6 | 21.0 | 18.2 | 19.6 | 13.7 | 18.2 |
| Cocoyl Sarcosinic Acid | | | | 2.0 | 2.0 | |
| Propylene Glycol | 12.0 | 10.0 | 12.0 | 12.0 | 12.0 | 12.0 |
| PEG-12 | | | 7.0 | 7.0 | 8.0 | 8.0 |
| Glycerin | 7.2 | 5.0 | 5.5 | 5.5 | 6.0 | 6.0 |
| Sorbitol | | | | | 4.2 | 4.2 |
| Cocamide DEA | | 9.0 | 8.0 | 8.0 | 8.0 | 8.0 |
| Capramide DEA | | | | | 4.0 | 4.0 |
| PEG-60 Almond Glyceride | | | | 5.0 | | |
| Behenamidopropyl PG Dimonium Chloride | | | | | | |
| Alkyl Polyglycoside Plantaren 2000 (50%) | | | | 4.6 | | |
| Polyquaternium-7 | | | | | | |
| Water | 17.0 | 17.0 | 18.8 | 14.5 | 15.1 | 15.3 |
| Cocamide DEA | 15.0 | 8.0 | 8.0 | 8.0 | | |
| Cocoyl Sarcosinate | | | | | | |
| PEG-6 | 7.2 | 9.0 | | | | |
| Citric Acid | | 1.0 | 0.4 | 0.4 | | |
| Isostearamidopropyl Morpholine Lactate | 2.0 | | | | | |
| Lauramidopropyl PG Dimonium Chloride | | | | 2.1 | | |
| Dye, Perfume, etc. | | | | | 1.0 | 1.0 |
| Mildness Score | 2.40 | 2.05 | 2.00 | 1.80 | 1.42 | 1.21 |

TABLE VI

| INGREDIENT | W178 | W199 | W203 | W217 | W220 | W218 |
|---|---|---|---|---|---|---|
| Sodium Stearate | | | | | | |
| Stearic Acid | 16.5 | 16.5 | 16.5 | 16.5 | 16.5 | 16.5 |
| Capric Acid | 2.0 | 2.0 | 2.0 | 2.0 | 2.0 | 2.0 |
| Sodium Hydroxide | 2.9 | 2.9 | 2.9 | 2.9 | 2.9 | 2.9 |
| Na Laureth-3 Sulfate | 16.1 | 18.2 | 18.2 | 15.4 | 17.5 | 17.5 |
| Cocoyl Sarcosinic Acid | 2.0 | 2.0 | 2.0 | 4.7 | 1.7 | 2.0 |
| Propylene Glycol | 12.0 | 10.7 | 11.1 | 12.0 | 12.0 | 12.0 |
| PEG-12 | 8.0 | 7.0 | 7.4 | 6.6 | 6.9 | 8.0 |
| Glycerin | 6.0 | 5.2 | 5.6 | 5.0 | 5.2 | 6.0 |
| Sorbitol | 4.2 | 3.6 | 3.9 | 3.5 | 3.6 | 4.2 |
| Cocamide DEA | 8.0 | 8.0 | .0 | 6.6 | 6.9 | 8.0 |
| Capramide DEA | 4.0 | 4.0 | 4.0 | 3.3 | 3.4 | 4.0 |
| PEG-60 Almond Glyceride | | | 5.0 | 3.0 | 3.0 | |
| Behenamidopropyl PG Dimonium Chloride | | 2.0 | | 0.9 | 0.9 | |
| Alkyl Polyglycoside Plantaren 2000 (50%) | | | | 1.0 | 1.0 | |
| Polyquaternium-7 | | | | 0.04 | 0.04 | |
| Water | 14.3 | 16.9 | 12.4 | 15.6 | 15.5 | 15.5 |
| Pluronic F108 | 3.0 | | | | | |
| Chondroitin Sulfate (and) Hydrolyzed Protein | | | | | | 0.4 |
| Dye, Perfume, Etc. | 1.0 | 1.0 | 1.0 | 1.0 | 1.0 | 1.0 |
| Mildness Score | 0.95 | 1.05 | 0.89 | 1.50 | 1.45 | 1.25 |

TABLE VII

| INGREDIENT | W222 | W210 | W233 | W231 | W235 | W234 |
|---|---|---|---|---|---|---|
| Sodium Stearate | | | | | | |
| Stearic Acid | 16.5 | 16.5 | 16.8 | 16.5 | 16.5 | 16.5 |
| Capric Acid | 2.0 | 2.0 | 2.0 | 2.0 | 2.0 | 2.0 |
| Sodium Hydroxide | 2.9 | 2.9 | 2.0 | 4.6 | 2.9 | 2.9 |
| Na Laureth-3 Sulfate | 17.5 | 17.5 | 17.9 | 12.5 | 17.5 | 17.5 |
| Cocoyl Sarcosinic Acid | 2.0 | 1.7 | 1.7 | 1.7 | 1.7 | 1.7 |
| Propylene Glycol | 12.0 | 12.0 | 12.2 | 12.0 | 12.0 | 12.0 |
| PEG-12 | 8.0 | 6.9 | 7.0 | 6.5 | | |
| Glycerin | 6.0 | 5.2 | 5.3 | 4.9 | 5.2 | 5.2 |
| Sorbitol | 4.2 | 3.6 | 3.7 | 3.4 | 3.6 | 3.6 |
| Cocamide DEA | 8.0 | 6.9 | 7.0 | 6.8 | 6.9 | 6.9 |
| Capramide DEA | 4.0 | 3.4 | 3.5 | 3.4 | 3.4 | 3.4 |
| PEG-60 Almond Glyceride | | 3.0 | 3.1 | 3.0 | 3.0 | 3.0 |
| Behenamidopropyl PG Dimonium Chloride | | 0.9 | 0.9 | 0.9 | 0.9 | 0.9 |
| Alkyl Polyglycoside Plantaren 2000 (50%) | | 1.0 | 1.0 | 1.0 | 1.0 | 1.0 |
| Polyquaternium-7 | | 0.04 | 0.04 | 0.04 | 0.04 | 0.04 |
| Water | 13.9 | 15.5 | 14.9 | 14.8 | 15.5 | 15.5 |
| Hydrolyzed Animal Protein | 2.0 | | | | | |
| Lauryl Phosphoric Acid | | | | 5.0 | | |
| PPG-5-Laureth-5 | | | | | | 6.9 |
| PPG-2-Ceteareth-9 | | | | | 6.9 | |
| Dye, Perfume, etc. | 1.0 | 1.0 | 1.0 | 1.0 | 1.0 | 1.0 |
| Mildness Score | 1.15 | 1.05 | 2.65 | 2.40 | 1.90 | 1.65 |

TABLE VIII

| INGREDIENT | W210 | W241 | W238 | W239 | W234 |
|---|---|---|---|---|---|
| Sodium Stearate | | | | | |
| Stearic Acid | 16.5 | 16.5 | 16.5 | 16.5 | 16.5 |
| Capric Acid | 2.0 | 2.0 | 2.0 | 2.0 | 2.0 |
| Sodium Hydroxide | 2.9 | 2.9 | 2.9 | 2.9 | 2.9 |
| Na Laureth-3 Sulfate | 17. | 17.5 | 17.5 | 17.5 | 17.5 |
| Cocoyl Sarcosinic Acid | 1.7 | 1.5 | 1.5 | 1.5 | 1.7 |
| Propylene Glycol | 12.0 | 12.0 | 12.0 | 12.0 | 12.0 |
| PEG-12 | 6.9 | 6.1 | 6.1 | 6.1 | |
| Glycerin | 5.2 | 4.7 | 4.7 | 4.7 | 5.2 |
| Sorbitol | 3.6 | 3.3 | 3.3 | 3.3 | 3.6 |
| Cocamide DEA | 6.9 | 6.1 | 6.1 | 6.1 | 6.9 |
| Capramide DEA | 3.4 | 3.0 | 3.0 | 3.0 | 3.4 |
| PEG-60 Almond Glyceride | 3.0 | 3.0 | 3.0 | 3.0 | 3.0 |
| Behenamidopropyl PG Dimonium Chloride | 0.9 | 0.9 | 0.9 | 0.9 | 0.9 |
| Alkyl Polyglycoside Plantaren 2000 (50%) | 1.0 | 1.0 | 1.0 | 1.0 | 1.0 |
| Polyquaternium-7 | 0.04 | 0.04 | 0.04 | 0.04 | 0.04 |
| Water | 15.5 | 15.5 | 17.0 | 15.5 | 15.5 |
| dl-Panthenol | 15.5 | 15.5 | 17.0 | 15.5 | 15.5 |
| Sodium Isostearoyl Lactylate | | | | 3.0 | |
| Hydrolyzed Wheat Protein | | | 1.5 | | |
| Dye, Perfume, etc. | 1.0 | 1.0 | 1.0 | 1.0 | 1.0 |
| Mildness Score | 1.21 | 1.05 | 1.00 | 0.95 | 0.89 |

It should be noted that the mildness scores can vary depending on the time of year and the geographic area where the tests are run. Furthermore, the mildness scores of the bars in Tables IV–VIII were compared to the scores obtained on commercially available products, and particularly those products that are known to have a reputation for being relatively mild, such as "Dove" cleansing bar. "Ivory" bar soap was used as a control for a so-called "irritating" product.

It is helpful in appreciating mildness scores to understand that such scores can vary rather considerably depending on the time of the year and other factors. For example, it was found that the mildness scores of Dove cleansing bar as conducted over a period of more than one year varied from 1.05 to as high as 2.65. Thus, whenever the bars of this invention were evaluated, the mildness of both the Dove and Ivory products was also evaluated.

The following Table IX summarizes the mildness scores of various bar compositions of this invention and scores for each of the "Dove" and "Ivory" products.

TABLE IX

| BAR | August Score | Nov. Score | March Score | October Score | Dec. Score | March Score | July Score |
|---|---|---|---|---|---|---|---|
| Dove | 1.29 | 2.4 | 2.25 | 1.05 | 1.85 | 2.65 | 1.16 |
| Ivory | 2.63 | 3.5 | 4.30 | 2.26 | 3.00 | | 2.89 |
| W11 | 0.99 | | | | | | |
| W18 | 0.99 | | | | | | |
| W22 | 1.03 | | | | | | |
| W24 | 1.18 | | | | | | |
| W55 | | 2.5 | | | | | |
| W70 | | 2.4 | | | | | |
| W105 | | | 2.40 | | | | |
| W102 | | | 2.05 | | | | |
| W124 | | | 2.00 | | | | |
| W114 | | | 1.80 | | | | |
| W190 | | | | 1.42 | | | |
| W172 | | | | 1.21 | | | |
| W199 | | | | 1.05 | | | |
| W178 | | | | 0.95 | | | |
| W203 | | | | 0.89 | | | |
| W217 | | | | | 1.50 | | |
| W220 | | | | | 1.45 | | |
| W218 | | | | | 1.25 | | |
| W222 | | | | | 1.15 | | |
| W210 | | | | | 1.05 | | |
| W233 | | | | | | 2.65 | |
| W231 | | | | | | 2.40 | |
| W235 | | | | | | 1.90 | |
| W234 | | | | | | 1.65 | |
| W210 | | | | | | | 1.21 |
| W241 | | | | | | | 1.05 |
| W238 | | | | | | | 1.00 |
| W239 | | | | | | | 0.95 |
| W234 | | | | | | | 0.95 |

In reviewing this chart, it should be noted that the raw mildness scores taken in August reveal that bars W11, W18, W22 and W24 were lower than either the Dove or Ivory bars. In the November scores, bars W55 and W70 were about on par with the Dove bar and lower than the Ivory bar.

What is claimed is:

1. A transparent cleansing bar composition consisting essentially of:

a) from about 10 to about 45% by weight of a synthetic detergent with about 15% to about 35% by weight of said detergent being a salt of a sulfated ethoxylated long chain alkyl alcohol of the formula R—(OCH$_2$CH$_2$)n-O—SO$_3$X wherein R is an alkyl group having from 12–16 carbon atoms, n is 2 or 3, and x is an alkali metal or alkaline earth metal;

b) from about 10 to about 30% by weight of a polyhydric alcohol selected from propylene glycol, glycerol and sorbitol and a polyethylene glycol of the formula H(OCH$_2$CH$_2$)n OH wherein n has an average value of 6 to 16, and wherein said polyhydric alcohol and said polyethylene glycol are present in an amount in excess of the amount of soap in said compositions;

c) from about 17 to about 30% by weight of a water soluble soap, said soap being the reaction product of long chain fatty acids with an alkali and wherein the ratio of said water soluble soap to said synthetic detergent ranges from about 1:1 to about 1:2;

d) from about 5 to about 20% by weight of a fatty acid alkanolamide, e) from 0 to about 15% by weight of an alkyl sarcosinic acid of the formula

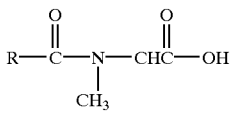

where R is alkyl having 10 to 16 carbon atoms:

f) from 0 to about 10% by weight of a nonionic alkyl polyglycoside of the formula:

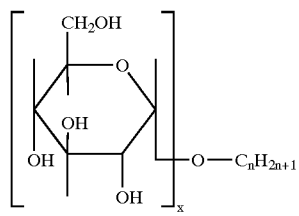

X is greater than 1 and less than 2; and g) wherein said composition has a pH of not less than about 8.0, contains at least about 17% by weight of said soap and is substantially free of monohydric and dihydric alcohols.

2. The composition of claim 1 wherein R is lauroyl in said sulfated ethoxylated long chain alkyl alcohol and X is sodium.

3. The composition of claim 2 wherein the amount of fatty acid alkanolamide present is from about 10–15 weight % of said composition.

4. The composition of claim 3 wherein said water soluble soap is formed in situ by the reaction of long chain fatty acids with an alkali.

5. The composition of claim 4 wherein the ratio of said alcohol to said soap is about at least 1.25 parts of alcohol to about 1 part of soap.

6. The composition of claim 5 wherein the amount of soap present is at least 18 weight %.

7. The composition of claim 6 which contains from about 1.0 to about 3.0 weight % of said polyglycoside.

8. The composition of claim 7 which contains from about 5 to about 10 weight % of said alkyl sarcosinic acid.

9. The composition of claim 8 which additionally contains a skin benefiting agent selected from the group consisting of hydrolyzed animal protein octyl methoxycinnamate, dimethicone copolyol, vitamin E linoleate, and capric triglyceride.

10. The composition of claim 9 wherein said agent is present in an amount ranging from about 0.5 to about 3 weight % of the composition.

* * * * *